United States Patent [19]
Kanai et al.

[11] Patent Number: 4,922,910
[45] Date of Patent: May 8, 1990

[54] CANNULA HAVING AN ELECTRODE

[75] Inventors: Naritoshi Kanai, Tokyo; Akira Suzuki, Nishio, both of Japan

[73] Assignees: Aisin Seiki Kabushiki Kaisha, Aichi; Kabushiki Kaisha Shisangyokaihatsu, Tokyo, both of Japan

[21] Appl. No.: 241,276

[22] Filed: Sep. 7, 1988

[30] Foreign Application Priority Data

Sep. 7, 1987 [JP] Japan .................. 62-223719

[51] Int. Cl.⁵ .............................................. A61B 5/04
[52] U.S. Cl. .................................... 128/642; 600/17
[58] Field of Search ...................... 128/642, 784–786, 128/419 P, 692; 604/21; 600/17; 623/25

[56] References Cited

U.S. PATENT DOCUMENTS

| | | | |
|---|---|---|---|
| 3,807,391 | 4/1974 | Bolduc | 604/21 X |
| 4,352,360 | 10/1982 | King | 128/786 |
| 4,644,960 | 2/1987 | Johans | 128/786 |

FOREIGN PATENT DOCUMENTS

| | | | |
|---|---|---|---|
| 0157394 | 10/1985 | European Pat. Off. | 128/642 |
| 1937137 | 2/1970 | Fed. Rep. of Germany | 128/642 |
| 2604165 | 8/1976 | Fed. Rep. of Germany | 128/419 P |
| 2822829 | 11/1979 | Fed. Rep. of Germany | 128/786 |

Primary Examiner—Lee S. Cohen
Attorney, Agent, or Firm—Sughrue, Mion, Zinn, Macpeak & Seas

[57] ABSTRACT

A cannula has an electrode therein for detecting electrocardiographic signals. The electrode is located in the inner wall of the cannula and has anti-thrombus characteristics. The electrode comprises a composition of an anti-thrombus polyurethane powder and a carbon powder. This composition has electrically conductive and anti-thrombus characteristics. The electrode is located in a recess of the inner wall of the cannula. The electrode is connected to the outside through a wire conductor.

20 Claims, 6 Drawing Sheets

CANNULA HAVING AN ELECTRODE

BACKGROUND OF THE INVENTION

The present invention relates to a cannula having an electrode for detecting an intraortic electrocardiographic signal which can be used for example, in an artificial heart apparatus, a pulsatile artificial heart-lung apparatus, a pulsatile bypass pump apparatus, a vein-vein bypass apparatus, PTCA, etc. for synchronous operation with the pulsation of a natural heart.

It is important for an artificial heart which is connected in parallel to a natural heart to pump blood with a pulsation synchronous to a natural heartbeat. It is well known in the art that an electrocardiogram is provided by comparing voltage differences between plural electrodes stuck on the body. However, such electric signals may have some drawbacks.

Such electric signals include both electrocardiographic signals and electromyographic signals and accordingly, there may be a disturbance of the electrocardiogram caused by movement of the patient. The voltage level of such an electrocardiographic signal may be low and therefore the S/N ratio is low. Thus, detection of the electric signals may be difficult. Signal components may vary in accordance with the positions of electrodes and therefore, some skill may be required to place the electrodes on a patient's body.

SUMMARY OF THE INVENTION

Accordingly, one of the objects of the present invention is to produce an electrode to obviate the above drawbacks.

To achieve the above object, and in accordance with the principles of the invention as embodied and broadly described herein, a cannula is provided with at least one electrode which is located in the inner wall of the cannula in order to detect an electrocardiographic signal and which has an anti-thrombus characteristic.

When used with an artificial heart apparatus, a pulsatile artificial heart-lung apparatus, a pulsatile bypass pump apparatus, a vein-vein bypass apparatus, PTCA, etc., one end of the cannula is connected to a vein or an artery near the natural heart and the other end of the cannula is connected to such apparatus and blood is passed to the natural heart through the cannula. Because the end of the cannula which is connected to a vein or an artery is close to the natural heart, there is a voltage difference including an electrocardiographic signal in the blood passing through such portion of the cannula. Accordingly, an electrocardiographic signal can be detected from the voltage changes which are detected by at least one electrode located in the inner wall of the cannula. However, in such a cannula it is important to protect against the formation of a thrombus which may be caused in the cannula and the electrode should have an anti-thrombus characteristic in addition to being electrically conductive.

Generally, an anti-thrombus substance has electrical insulating characteristics and ordinary electrodes may cause a thrombus or change the characteristics of the blood. Therefore, a preferred embodiment of this invention uses an electrode comprised of a composition of anti-thrombus polyurethane powder and carbon powder. This composition has electrically conductive and anti-thrombus characteristics.

BRIEF DESCRIPTION OF THE DRAWINGS

For a full understanding of the true scope of the invention, the following detailed description should be read in conjunction with the drawings, wherein.

DETAILED DESCRIPTION OF THE PREFERRED EMBODIMENTS

In the following, preferred embodiments of the present invention will be described with reference to the drawings.

Figure 1:
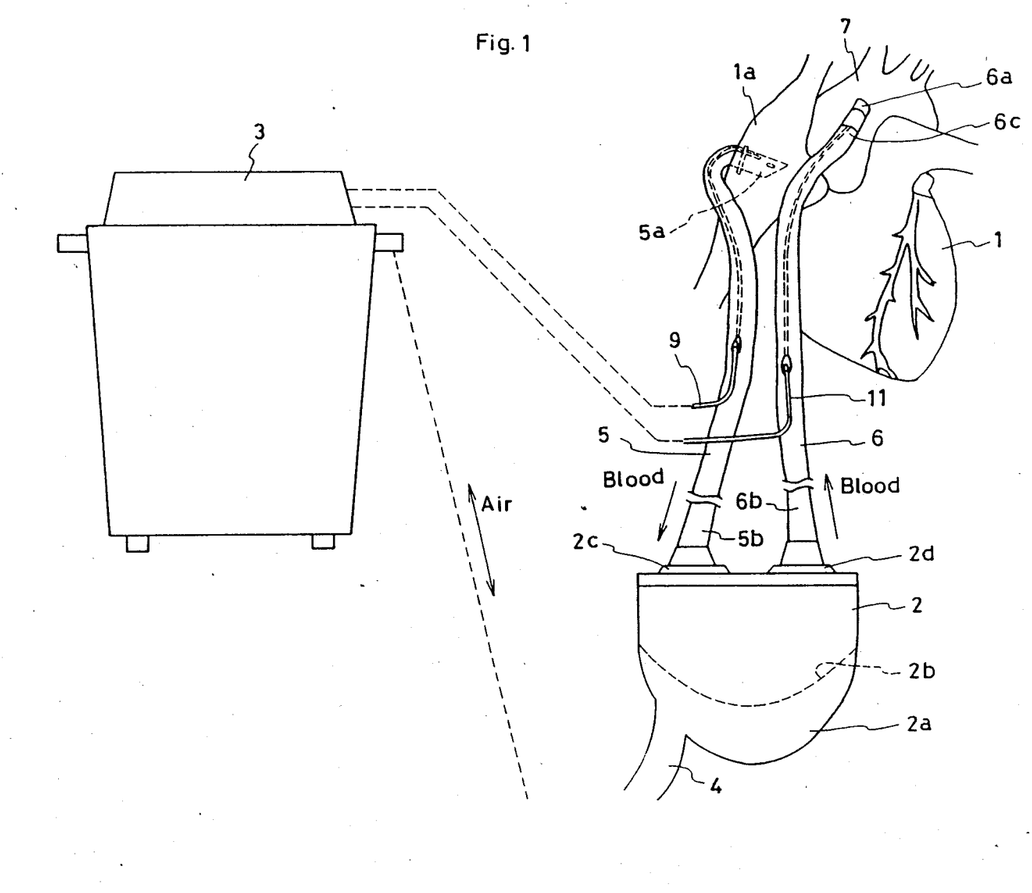
FIG. 1 is a diagram showing an artificial heart pump system suing a cannula according to the present invention.

FIG. 1 illustrates an artificial heart pump system using a cannula according to the present invention wherein 1 is a natural heart, 2 is an artificial heart pump and 3 is an artificial heart pump driving apparatus. An air tube 4 is connected between an air chamber 2a of the artificial heart pump 2 and the driving apparatus 3. Air in the chamber 2a is periodically pumped by the driving apparatus 3 through the air tube 4. According to the volume changes of air in the air chamber 2a, a diaphragm 2b moves periodically and blood is circulated from an inlet 2c to an outlet 2d of the artificial heart pump 2. Designated at 5 and 6 are cannulas which connect the artificial heart pump to the natural heart. One end 5a of the blood drawing cannula 5 is connected to the left atrium 1a of the natural heart 1 and the other end 5b is connected to the inlet 2c of the artificial heart pump 2. One end 6a of the blood supplying cannula 6 is connected to an aorta 7 and the other end 6b is connected to the outlet 2d of the artificial heart pump 2.

Figure 2:
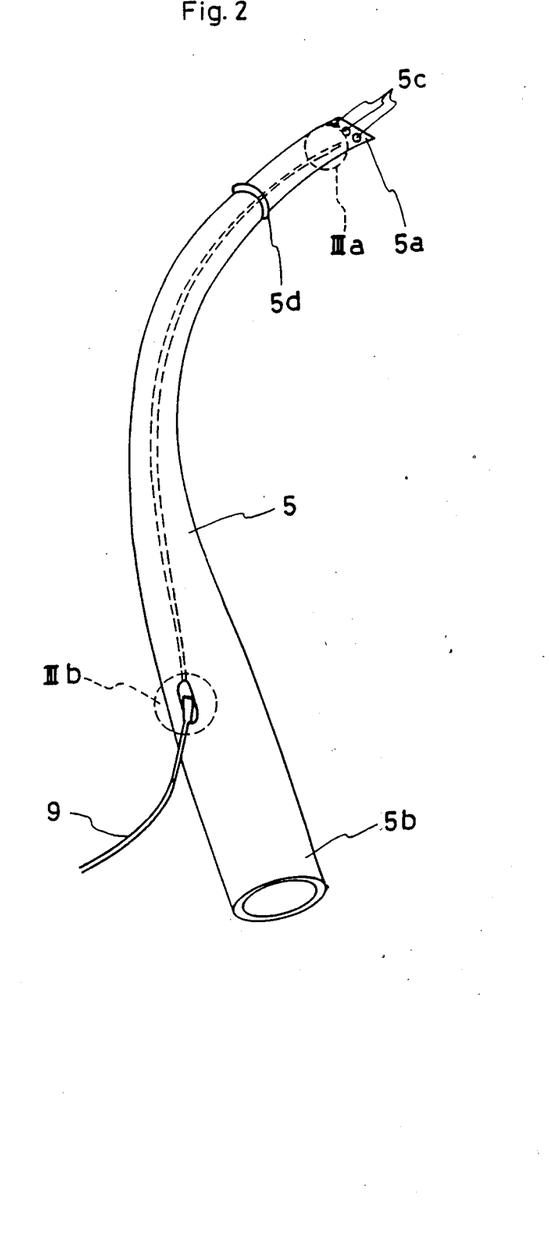
FIG. 2 is a perspective view showing a cannula according to the invention.

FIG. 2 shows the external appearance of the cannula 5 wherein the cannula is made of a tubular shape. The end 5a is cut on the slant and has plural holes 5c connecting the inside and outside. These holes prevent the blood flow from stopping if the opening of the cannula 5 is closed by movement of the left atrium of the natural heart 1. Adjacent to the end 5a of the cannula 5 there is provided a flange 5d which prevents the cannula 5 from separating from the natural heart 1. When the cannula 5 is attached to the natural heart 1, a wall of the left atrium is cut open and the end 5a of the cannula 5 is inserted into the opening of the left atrium until the flange 5d is inside the left atrium. Then the opening of the left atrium is closed by stitches. Accordingly, the end 5a of the cannula 5 is prevented from separating from the left atrium. In this embodiment, the end 5a of the cannula 5 has an inside diameter of about 10 mm and the other end 5b has an inside diameter of about 16 mm. The thickness of the cannula 5 is about 2 mm at the thickest portion. Almost all of the cannula 5 is made of an anti-thrombus polyurethane substance.

Figure 3A:
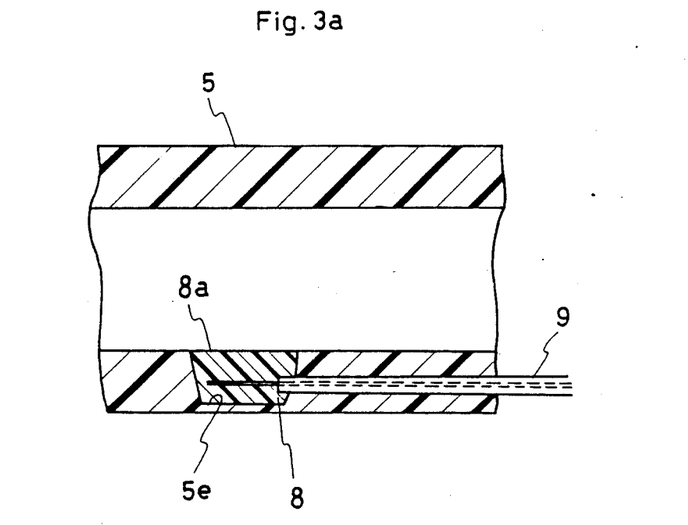
FIGS. 3a and 3b are sectional views showing parts of a cannula according to the invention.

FIG. 3a shows a sectional view of a part of the cannula 5 which is indicated at IIIa in FIG. 2. Referring to FIG. 3a, a small recess 5e is provided in the wall of the cannula 5 and an electrically conductive substance 8 fills the recess 5e. This electrical conductor 8 is composed especially to provide electrically conductive and anti-thrombus characteristics. In this embodiment, carbon powder (diameter of a carbon particle being about 0.01 $\mu$m) is combined with an anti-thrombus polyurethane substance. A combined ratio of carbon is 45% (weight %). A lead wire 9 is provided inside the wall of the cannula 5. The insulation of the terminal 9a of the lead 9 is peeled off and the peeled portion is located at the conductor 8 in the recess 5e and connected with the conductor 8 both electrically and mechanically. In this embodiment, the electrical resistance between the surface 8a of the electric conductor 8 and the lead wire 9 is less than 100 $\Omega$. The lead wire 9 is elongated along the axis of the cannula 5 and extends out from the cannula 5 at IIIb ahead of the terminal portion 5b of the cannula 5. Though the terminal portion 5b may be cut for adjusting a length of cannula 5 within a patient when the cannula 5 and the artificial heart pump are attached, there is little chance of cutting the lead wire 9 in addition to the terminal portion 5b of the cannula 5 because the lead wire is pulled out ahead of the terminal end of the cannula 5.

Figure 3B:
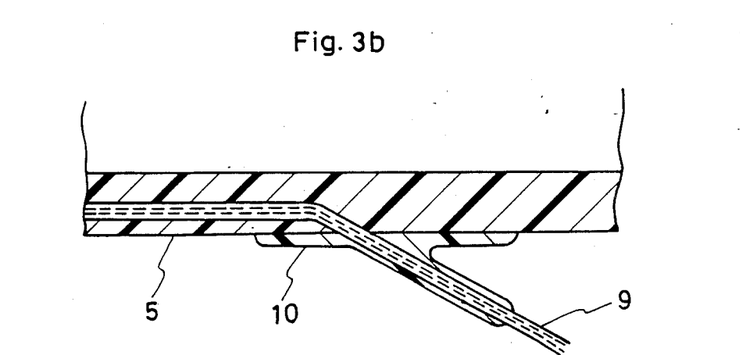

FIG. 3b shows a sectional view of a part of the cannula 5 which is indicated by IIIb in FIG. 2. Referring to FIG. 3b, the lead wire 9 extends out from the inside of the wall to the outside of the cannula 5. At the position where the wire is pulled out a urethane adhesive 10 is applied for fixing the wire 9 to the cannula 5 and for reinforcement of the wire 9. The terminal end of the wire 9 is connected to the artificial heart pump apparatus 3 through a connector (not shown). The other cannula 6 is also provided with an electrode inside the wall of the cannula. A lead wire 11 which is connected to the electrode extends out from the cannula 6 and connected to the artificial heart pump apparatus 3 as shown in FIG. 1. Because the cannula 6 is connected to an artery 7, an artificial blood pipe 6a is attached to the cannula 6. An electrode cannot be located in the artificial blood pipe. Therefore, the electrode is located at the inner wall of the tip 6c which is made of polyurethane.

Figure 4A:
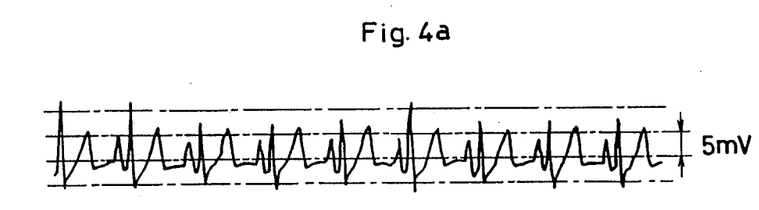
FIGS. 4a and 4b are wave forms showing electrocardiograms which were provided by an electrode in a cannula according to the invention and by an electrode attached on the skin of a patient.
Figure 4B:
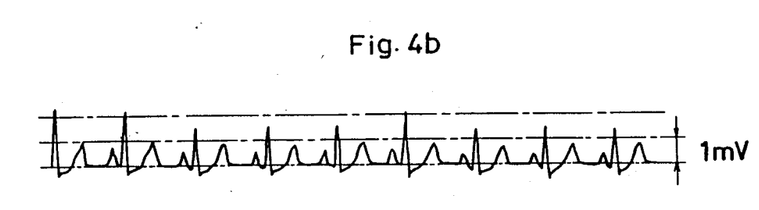

FIG. 4a shows an electrical wave form, an EKG signal, which appears between the lead wire 9 of the cannula 5 and the lead wire 11 of the cannula 6. FIG. 4b shows an electrical wave form which is obtained from two electrodes on a patient's body. Referring to FIGS. 4a and 4b, the voltage levels detected by the electrodes located in the cannulas are about ten times as large as the voltage levels detected by the electrodes located on the body. As to electrical signals from the electrodes of the cannulas, because these electrodes detect voltages at a closer position to the natural heart, there are very few electromyographic signals which are caused by muscles other than the heart. Therefore, processing of the electric signals is easy. In this embodiment voltages are detected by the electrodes located at each of the cannulas, however, even if the voltages are detected between one electrode of a cannula and an electrode on the patient, electrical signals are better than signals detected in the conventional manner.

FIGS. 5a, 5b, 5c and 5d show different embodiments of the invention, especially with respect to recesses 5e in the cannula 5 in which the electrodes are located. In this embodiment of FIG. 5a, the electrode has high anti-thrombus characteristics to prevent a thrombus even if anti-thrombus medication, for example "HEPARIN" is not given to the patient.

Figure 5A:
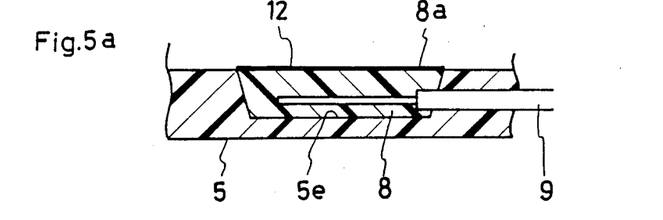
FIGS. 5a, 5b, 5c, and 5d are sectional views of different embodiments of electrodes in a cannula according to the invention.

Another electrical conductor 12 is provided on the surface 8a of the electrical conductor 8. The additional conductor 12 is also a mixture of anti-thrombus polyurethane powder and carbon powder. However, the percentage of carbon is less than that in the electrical conductor 8. Because this additional conductor 12 has low carbon content, this conductor has a high anti-thrombus characteristic and a low electrical conductivity. Therefore, in this embodiment the conductor 12 is dissolved in a solvent and painted thinly (about 10 $\mu$m thick). Thus the electrical resistance between the blood and the wire 9 is reduced.

Figure 5B:
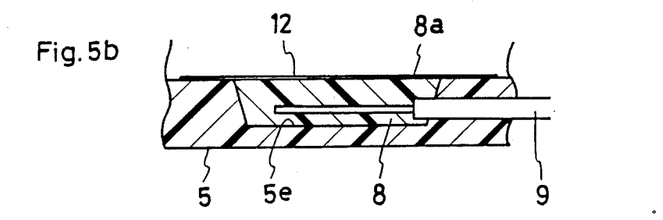

Referring to FIG. 5b, this embodiment also has an additional conductor 12 painted on the surface 8a of the conductor 8. However, in this embodiment, the conductor 12 covers beyond the recess 5e. Because the conductor 8 has a high ratio of carbon mixture, there is a low adhesiveness between the conductor 8 and the recess 5e of the cannula 5. Thus, there is a possibility that the conductor 8 may come out of the recess 5e. In this embodiment, the conductor 8 and the surrounding surface of the cannula are covered by the conductor 12 which has a better adhesiveness in order to prevent the conductor 8 from coming out of the recess 5e.

Figure 5C:
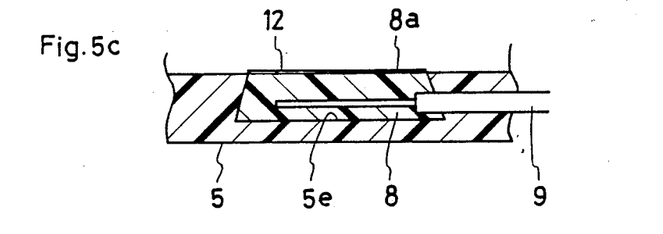

Referring to FIG. 5c in this embodiment there is provided a recess 5e' which has an opening narrower than it's bottom in order to prevent the conductor 8 from coming out.

Figure 5D:
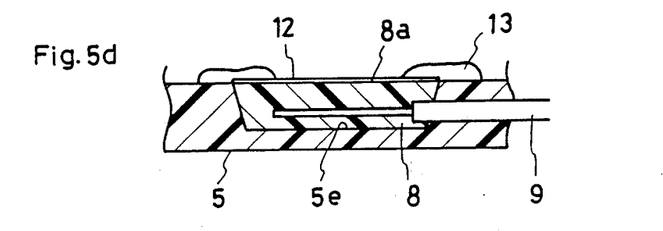

Referring to FIG. 5d in this embodiment the opening of the recess 5e is ringed by a layer of anti-thrombus polyurethane 13 which overlies the conductor 8 and the surrounding surface of the cannula to prevent the conductor 8 from coming out of the recess.

Figure 6:
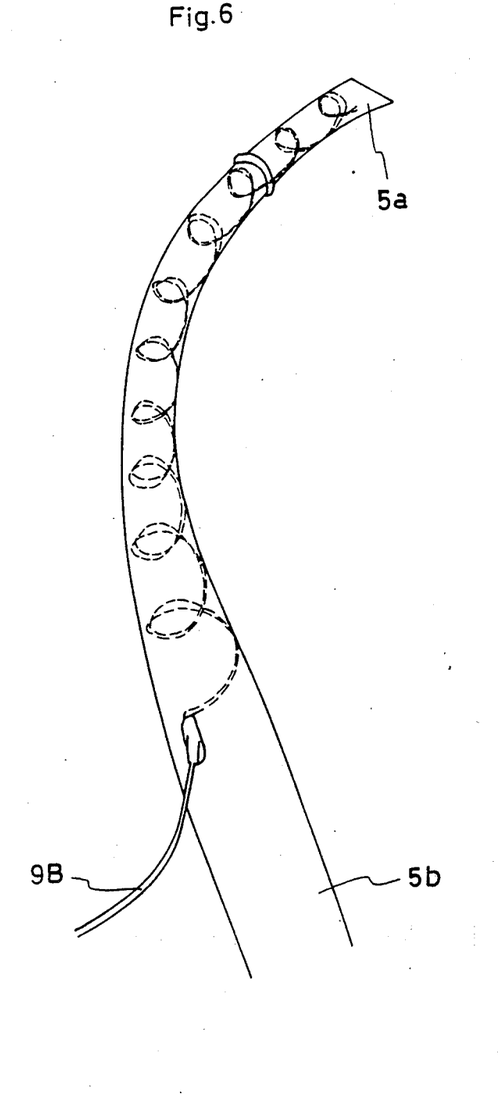
FIG. 6 is a perspective view of a cannula according to a different embodiment of the invention.

FIG. 6 shows a different embodiment of this invention. Referring to FIG. 6, the lead wire 9B which is connected with the electrode inside the cannula is made of a spiral construction. This allows the cannula to bend easily and prevents the wire from breaking when the cannula is bent.

The invention has been described in an illustrative manner and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

What is claimed is:

1. A cannula having an electrode comprising:
a tubular member comprised of an insulating-substance having one end which is adapted to be inserted in a blood vessel of a patient and another end adapted to be connected to a blood circulating apparatus, said tubular member having a flange adjacent said one end to prevent the separation of the cannula from the blood vessel,
electrode means for detecting an electrocardiographic signal secured in said tubular member on an inner wall of said tubular member and comprised of substances having anti-thrombus and electrically conductive characteristics; and electrical conductor means having one end secured to said electrode means for connecting said electrode means externally of said tubular member.

2. A cannula according to claim 1, wherein said electrode means is comprised of an anti-thrombus insulating substance and an electrically conductive substance.

3. A cannula according to claim 2, wherein said electrode means comprises two laminated parts which have different composition ratios of an anti-thrombus insulating substance and electrically conductive substance wherein one of said parts which includes less electrically conductive substance is thinner than the other part and is located in said inner wall of said tubular member.

4. A cannula according to claim 1, further comprising a recess located in said inner wall of said tubular member, wherein said electrode means is located in said recess of said tubular member.

5. A cannula according to claim 4, wherein said recess has a projection made of an anti-thrombus substance projecting into the interior of said tubular member about the circumference thereof.

6. A cannula according to claim 4, wherein said recess has a wider opening than the bottom thereof.

7. A cannula according to claim 1, wherein said electrical conductor means is a wire and said electrode means is located adjacent said one end of said tubular member with one end of said wire being connected to said electrode mans and the other end extending from a remote portion of said tubular member.

8. A cannula according to claim 7, wherein said wire is made of spiral construction in said inner wall of said tubular member.

9. A cannula having an electrode comprising:
a tubular member comprised of an insulating-substance having one end which is adapted to be inserted in a blood vessel of a patient and another end adapted to be connected to a blood circulating apparatus, said one end having a first inside diameter and said another end having a second inside diameter greater than said first inside diameter
electrode means for detecting an electrocardiographic signal secured in said tubular member on an inner wall of said tubular member and comprised of substances having anti-thrombus and electrically conductive characteristics; and
electrical conductor means having one end secured to said electrode means for connecting said electrode means externally of said tubular member.

10. A cannula according to claim 9, wherein said electrode means is comprised of an anti-thrombus insulating substance and an electrically conductive substance.

11. A cannula according to claim 10, wherein said electrode means comprises two laminated parts which have different composition ratios of an anti-thrombus insulating substance and electrically conductive substance wherein one of said parts which includes less electrically conductive substance is thinner than the other part and is located in said inner wall of said tubular member.

12. A cannula according to claim 9, further comprising a recess located in said inner wall of said tubular member, wherein said electrode means is located in said recess of said tubular member.

13. A cannula according to claim 12, wherein said recess has a projection made of an anti-thrombus substance projecting into the interior of said tubular member about the circumference thereof.

14. A cannula according to claim 12, wherein said recess has a wider opening than the bottom thereof.

15. A cannula according to claim 9, wherein said electrical conductor means is a wire and said electrode means is located adjacent said one end of said tubular member with one end of said wire being connected to said electrode mans and the other end extending from a remote portion of said tubular member.

16. A cannula according to claim 15, wherein said wire is made of spiral construction in said inner wall of said tubular member.

17. A cannula having an electrode comprising:
a tubular member comprised of an insulating substance having one end which is adapted to be inserted in a blood vessel of a patient and another end adapted to be connected to a blood circulating apparatus;
electrode means for detecting an electrocardiographic signal secured in said tubular member on an inner wall of said tubular member;
said electrode means being comprised of two laminated parts having different composition ratios of anti-thrombus insulating substance and an electrically conductive substance wherein one of said parts which includes less electrically conductive substance is thinner than the other part and is located in said inner wall of said tubular member, and
electrical conductor means having one end secured to said electrode means for connecting said electrode means externally of said tubular member.

18. A cannula having an electrode comprising:
a tubular member comprised of an insulating substance having one end which is adapted to be inserted in a blood vessel of a patient and another end adapted to be connected to a blood circulating apparatus;
electrode means for detecting an electrocardiographic signal secured in said tubular member on an inner wall of said tubular member and comprised of substances having anti-thrombus and electrically conductive characteristics,
electrical conductor means having one end secured to said electrode means for connecting said electrode means externally of said tubular member; and
a recess located in said inner wall of said tubular member and having a projection made of an anti-thrombus substance projecting into the interior of said tubular member about the circumference thereof with said electrode means being located in said recess of said tubular member.

19. A cannula having an electrode comprising:
a tubular member comprised of an insulating substance having one end which is adapted to be inserted in a blood vessel of a patient and another end adapted to be connected to a blood circulating apparatus;
electrode means for detecting an electrocardiographic signal secured in said tubular member on an inner wall of said tubular member and comprised of substances having anti-thrombus and electrically conductive characteristics,
electrical conductor means having one end secured to said electrode means for connecting said electrode means externally of said tubular member; and
a recess located in said inner wall of said tubular member with said electrode means being located in said recess of said tubular member, said recess having a wider opening than the bottom thereof.

20. A cannula-blood pipe combination having an electrode comprising:

a tubular member comprised of an insulating substance having one end which is adapted to be inserted in a blood vessel of a patient and another end adapted to be connected to a blood circulating apparatus;

an artificial blood pipe connected to said one end of said tubular member, electrode means for detecting an electrocardiographic signal secured in said tubular member adjacent said one end thereof; and electrical conductor means having one end secured to said electrode means for connecting said electrode means externally of said tubular member.

* * * * *

UNITED STATES PATENT AND TRADEMARK OFFICE
CERTIFICATE OF CORRECTION

PATENT NO. : 4,922,910
DATED : May 8, 1990
INVENTOR(S) : Naritoshi KANAI and Akira SUZUKI It is certified that error appears in the above-identified patent and that said Letters Patent is hereby corrected as shown below:

On the title page, Item [73], change "Shisangyokaihatsu" to

-- Shinsangyokaihatsu --

Signed and Sealed this

Twelfth Day of May, 1992

Attest:

DOUGLAS B. COMER

*Attesting Officer*  *Acting Commissioner of Patents and Trademarks*